US005952546A

United States Patent [19]
Bedbrook et al.

[11] Patent Number: 5,952,546
[45] Date of Patent: Sep. 14, 1999

[54] DELAYED RIPENING TOMATO PLANTS WITH T-DNA BEARING A TRUNCATED ACC2 SYNTHASE GENE

[75] Inventors: John R. Bedbrook; Pamela Dunsmuir, both of Piedmont; William J. Howie, Concord; Lawrence K. Joe; Kathleen Y. Lee, both of Oakland, all of Calif.

[73] Assignee: DNA Plant Technology Corporation, Oakland, Calif.

[21] Appl. No.: 08/673,768

[22] Filed: Jun. 27, 1996

Related U.S. Application Data

[60] Provisional application No. 60/000,721, Jun. 30, 1995.
[51] Int. Cl.⁶ .............................. A01H 5/00; C12N 5/14; C12N 15/29; C12N 15/52
[52] U.S. Cl. ................ 800/298; 435/320.1; 435/419; 435/468; 536/23.2; 536/23.6; 800/283; 800/317.4
[58] Field of Search .................. 536/23.2, 23.6; 435/172.3, 320.1, 419; 800/205, DIG. 44

[56] References Cited

U.S. PATENT DOCUMENTS

| | | |
|---|---|---|
| 5,283,184 | 2/1994 | Jorgensen . |
| 5,498,831 | 3/1996 | Burgess et al. ................ 800/205 |

FOREIGN PATENT DOCUMENTS

WO 92/04456   3/1992   WIPO .

OTHER PUBLICATIONS

Liang, et al., the 1–aminocyclopropane–1–carboxylate synthase gene family of *Arabidopsis thaliana*. Proc Nat'l Acad. Sci. USA 89:11046 (1992).

Rottman, et al., 1–Aminocyclopropane–1–Carboxylate Synthase in tomato is encoded by a multigene family whose transcription is induced during fruit and floral senescence. *J. Mol. Biol.* 222:937 (1991).

Van der Straeten, et al., Cloning, genetic mapping, and expression analysis of an *Arabidopsis thaliana* gene that encodes 1–aminocyclopropane–1–carboxylate synthase. *Proc. Nat'l Acad. Sci. USA* 89:9969 (1992).

Jorgensen, et al., T–DNA is organized predominantly in inverted repeat structures in plants transformed with *Agrobacterium tumefaciens* C58 derivatives. *Mol. Gen. Genet.* 207:471 (1987).

Stam M, et al. "The silence of genes in transgenic plants." Ann. Bot. 79:3–12, 1997.

Koziel MG, et al. "Optimizing expreSsion of transgenes with an emphasis on post–transcriptional events." Plant Mol. Biol. 32:393–405, 1996.

Smith CJS, et al. "Antisense RNA inhibition of polygalacturonase gene expression in transgenic tomatoes." Nature 334: 724–726, Aug. 25, 1988.

Oeller PW, et al. "Reversible inhibition of tomato fruit senescence by antisense RNA." Science 254: 437–439, Oct. 18, 1991.

*Primary Examiner*—Douglas W. Robinson
*Assistant Examiner*—Amy J. Nelson
*Attorney, Agent, or Firm*—Townsend and Townsend and Crew

[57] ABSTRACT

The present invention provides tomato plants exhibiting a delayed ripening phenotype. The plants of the invention comprise a T-DNA insert comprising a first sequence of from about nucleotide 149 to about nucleotide 1237 of a tomato Acc synthase gene and two inverted repeats of the first sequence. Integration of the T-DNA insert into the plant genome inhibits ethylene biosynthesis in the fruit.

14 Claims, 4 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 15397 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

```
CGACGGCCAG TGCCAAGCTT GCATGCCTGC AGGTCGATCT AGTAACATAG ATGACACCGC      60

GCGCGATAAT TTATCCTAGT TTGCGCGCTA TATTTTGTTT TCTATCGCGT ATTAAATGTA     120

TAATTGCGGG ACTCTAATCA TAAAAACCCA TCTCATAAAT AACGTCATGC ATTACATGTT     180

AATTATTACA TGCTTAACGT AATTCAACAG AAATTATATG ATAATCATCG CAAGACCGGC     240

AACAGGATTC AATCTTAAGA AACTTTATTG CCAAATGTTT GAACGATCTG CCCCTTGACT     300

CTAGAAACAA ACTCGAAACC AACCTGGCTC TTGACATTCA AACGAAGATC CAAGCGAGAC     360

GTTAAGCTTA ACATCGTTTA TAATAACTCT CCATAACGAC ATTTCGCTAT CGAAAGTCGA     420

TTCCCTTAAA AGTGGACGCA AATCCATCCA ACAAAAAAGC CCCGCATTAT TTTTCAAGCA     480

TTTAATTCCC ACTACTTCAA GTCCATTAGT AAAATGTTTG TGCCTTTTAC CTAACCTCAT     540

CGCGCTTTCT CTTAGAAAAT TATCGACGAA TTTTTCGTCC GATGGCATTG CCGCTAAAAA     600

ATATTGCGTT TGTGTAGATA CTAAACCGAA ACTCGACATT TTTCTAGCAC AATTAACGAC     660

ATCGTCGTTA AAAGAATATA TGATTCCGAC TCTAAATCCT GGTAACCCCA TGTCTTTTGA     720

AAGACTGTAG ACGATGTGAA CTAAATCTTT GTTGCAGTAA GTCATTTCCT GTTCATCGAG     780

GATTTCAGCT ATACTGACGA ATTGAGGCGT GTCAAAGACA GTGGCTGCGT AGATTTCGTC     840

ACAAACAAGG TGGATGTTGT GTTGGTTGGT GAAACTCAAG ACACTTTTCA GTGTGTCTTT     900

GTCCAAAGTG GTGCCCAATG GATTTGATGG ATTGGTCAAA ATCAAACCTT TTACTTTGAT     960

GTTTGATTTT TGTGCATTTT CATATGCTTC TTTTACTGCT TTTGAAGTAA TTTTGAAATT    1020

ATTGGAGCTC TCACAGTGAA TTGGAATAAG TTGTACTCCA GTTCTCCATC TTAAATCTCT    1080

GTTAAATGCT GGGTAGTATG GTGAAGGTAC TAAAAATGCA TCGCCAGGAT CAGCCAAACA    1140

AAATATAATT GTCTCATTAG CTCCAGTGGC ACCACCAGCC ATAACAACTC TTTCTGGATC    1200

AAATCTAACT CTTCCTCCTC TTGTTTTCTC CATAAATTTC GCAATCGCTT TTCTGAATTC    1260

AGGCAAGCCA TGATAATCTT GAAAGTTGGC AATGGCCTTG AATGATTTGA TTCCTTCAGA    1320

ACAAATTGAA CCTTTTGGGT TTCTCTTAAT CCAATCTTCT ATCAAGTCTA AACAAAGCTG    1380

ATTTTCTGCT AAACCCATGG TTTAATAAGA AGAGAAAAGA GTTCTTTTGT TATGGCTGAA    1440
```

-continued

```
GTAATAGAGA AATGAGCTCG AGCGTGTCCT CTCCAAATGA AATGAACTTC CTTATATAGA    1500

GGAAGGGTCT TGCGAAGGAT AGTGGGATTG TGCGTCATCC CTTACGTCAG TGGAGATGTC    1560

ACATCAATCC ACTTGCTTTG AAGACGTGGT TGGAACGTCT TCTTTTTCCA CGATGCTCCT    1620

CGTGGGTGGG GGTCCATCTT TGGGACCACT GTCGGCAGAG GCATCTTGAA TGATAGCCTT    1680

TCCTTTATCG CAATGATGGC ATTTGTAGGA GCCACCTTCC TTTTCTACTG TCCTTTCGAT    1740

GAAGTGACAG ATAGCTGGGC AATGGAATCC GAGGAGGTTT CCCGAAATTA TCCTTTGTTG    1800

AAAAGTCTCA ATAGCCCTTT GGTCTTCTGA GACTGTATCT TTGACATTTT TGGAGTAGAC    1860

CAGAGTGTCG TGCTCCACCA TGTTGACGAA GATTTTCTTC TTGTCATTGA GTCGTAAAAG    1920

ACTCTGTATG AACTGTTCGC CAGTCTTCAC GGCGAGTTCT GTTAGATCCT CGATTTGAAT    1980

CTTAGACTCC ATGCATGGCC TTAGATTCAG TAGGAACTAC CTTTTTAGAG ACTCCAATCT    2040

CTATTACTTG CCTTGGTTTA TGAAGCAAGC CTTGAATCGT CCATACTGGA ATAGTACTTC    2100

TGATCTTGAG AAATATGTCT TTCTCTGTGT TCTTGATGCA ATTAGTCCTG AATCTTTTGA    2160

CTGCATCTTT AACCTTCTTG GGAAGGTATT TGATCTCCTG GAGATTGTTA CTCGGGTAGA    2220

TCGTCTTGAT GAGACCTGCT GCGTAGGCCT CTCTAACCAT CTGTGGGTCA GCATTCTTTC    2280

TGAAATTGAA GAGGCTAACC TTCTCATTAT CAGTGGTGAA CATAGTGTCG TCACCTTCAC    2340

CTTCGAACTT CCTTCCTAGA TCGTAAAGAT AGAGGAAATC GTCCATTGTA ATCTCCGGGG    2400

CAAAGGAGAT CCCGGGTACC GAGCTCGAAT TCGTAATCAT GGTCATAGCT GTTTCCTGTG    2460

TGAAATTGTT ATCCGCTCAC AATTCCACAC AACATACGAG CCGGAAGCAT AAAGTGTAAA    2520

GCCTGGGGTG CCTAATGAGT GAGCTAACTC ACATTAATTG CGTTGCGCTC ACTGCCCGCT    2580

TTCCAGTCGG GAAACCTGTC GTGCCAGCTG CATTAATGAA TCGGCCAACG CGCGGGGAGA    2640

GGCGGTTTGC GTATTGGGCA GCGGCCGCTG TTACCCGGCC GCCGTGCTGG ACCGGGTTGA    2700

ATGGTGCCCG TAACTTTCGG TAGAGCGGAC GGCCAATACT CAACTTCAAG GAATCTCACC    2760

CATGCGCGCC GGCGGGAAC CGGAGTTCCC TTCAGTGAAC GTTATTAGTT CGCCGCTCGG    2820

TGTGTCGTAG ATACTAGCCC CTGGGGCCTT TTGAAATTTG AATAAGATTT ATGTAATCAG    2880

TCTTTTAGGT TTGACCGGTT CTGCCGCTTT TTTTAAAATT GGATTTGTAA TAATAAAACG    2940

CAATTGTTTG TTATTGTGGC GCTCTATCAT AGATGTCGCT ATAAACCTAT TCAGCACAAT    3000

ATATTGTTTT CATTTTAATA TTGTACATAT AAGTAGTAGG GTACAATCAG TAAATTGAAC    3060

GGAGAATATT ATTCATAAAA ATACGATAGT AACGGGTGAT ATATTCATTA GAATGAACCG    3120

AAACCGGCGG TAAGGATCTG AGCTACACAT GCTCAGGTTT TTTACAACGT GCACAACAGA    3180

ATTGAAAGCA AATATCATGC GATCATAGGC GTCTCGCATA TCTCATTAAA GCAGGGGGTG    3240

GGCGAAGAAC TCCAGCATGA GATCCCCGCG CTGGAGGATC ATCCAGCCGG CGTCCCGGAA    3300

AACGATTCCG AAGCCCAACC TTTCATAGAA GGCGGCGGTG GAATCGAAAT CTCGTGATGG    3360

CAGGTTGGGC GTCGCTTGGT CGGTCATTTC GAACCCCAGA GTCCCGCTCA GAAGAACTCG    3420

TCAAGAAGGC GATAGAAGGC GATGCGCTGC GAATCGGGAG CGGCGATACC GTAAAGCACG    3480

AGGAAGCGGT CAGCCCATTC GCCGCCAAGC TCTTCAGCAA TATCACGGGT AGCCAACGCT    3540

ATGTCCTGAT AGCGGTCCGC CACACCCAGC CGGCCACAGT CGATGAATCC AGAAAAGCGG    3600

CCATTTTCCA CCATGATATT CGGCAAGCAG GCATCGCCAT GGGTCACGAC GAGATCCTCG    3660

CCGTCGGGCA TGCGCGCCTT GAGCCTGGCG AACAGTTCGG CTGGCGCGAG CCCCTGATGC    3720

TCTTCGTCCA GATCATCCTG ATCGACAAGA CCGGCTTCCA TCCGAGTACG TGCTCGCTCG    3780

ATGCGATGTT TCGCTTGGTG GTCGAATGGG CAGGTAGCCG GATCAAGCGT ATGCAGCCGC    3840
```

```
CGCATTGCAT CAGCCATGAT GGATACTTTC TCGGCAGGAG CAAGGTGAGA TGACAGGAGA    3900

TCCTGCCCCG GCACTTCGCC AATAGCAGC CAGTCCCTTC CCGCTTCAGT GACAACGTCG     3960

AGCACAGCTG CGCAAGGAAC GCCCGTCGTG GCCAGCCACG ATAGCCGCGC TGCCTCGTCC    4020

TGCAGTTCAT TCAGGGCACC GGACAGGTCG GTCTTGACAA AAAGAACCGG GCGCCCCTGC    4080

GCTGACAGCC GGAACACGGC GGCATCGAG CAGCCGATTG TCTGTTGTGC CCAGTCATAG     4140

CCGAATAGCC TCTCCACCCA AGCGGCCGGA GAACCTGCGT GCAATCCATC TTGTTCAATC    4200

ATGCGAAACG ATCCTCATCC TGTCTCTTGA TCCAGATTAT TTGGATTGAG AGTGAATATG    4260

AGACTCTAAT TGGATACCGA GGGGAATTTA TGGAACGTCA GTGGAGCATT TTTGACAAGA    4320

AATATTTGCT AGCTGATAGT GACCTTAGGC GACTTTTGAA CGCGCAATAA TGGTTTCTGA    4380

CGTATGTGCT TAGCTCATTA AACTCCAGAA ACCCGCGGCT GAGTGGCTCC TTCAATCGTT    4440

GCGGTTCTGT CAGTTCCAAA CGTAAAACGG CTTGTCCCGC GTCATCGGCG GGGTCATAA     4500

CGTGACTCCC TTAATTCTCC GCTCATGATC CAGATTATTT GGATTGAGAG TGAATATGAG    4560

ACTCTAATTG GATACCGAGG GGAATTTATG GAACGTCAGT GGAGCATTTT TGACAAGAAA    4620

TATTTGCTAG CTGATAGTGA CCTTAGGCGA CTTTTGAACG CGCAATAATG GTTTCTGACG    4680

TATGTGCTTA GCTCATTAAA CTCCAGAAAC CCGCGGCTGA GTGGCTCCTT CAATCGTTGC    4740

GGTTCTGTCA GTTCCAAACG TAAAACGGCT TGTCCCGCGT CATCGGCGGG GTCATAACG    4800

TGACTCCCTT AATTCTCCGC TCATGATCAA GGCAGGATAT ATTCAATTGT AAATGGCTTC    4860

ATGTCCGGGA AATCTACATG GATCAGCAAT GAGTATGATG GTCAATATGG AGAAAAGAA    4920

AGAGTAATTA CCAATTTTTT TTCAATTCAA AAATGTAGAT GTCCGCAGCG TTATTATAAA    4980

ATGAAAGTAC ATTTTGATAA AACGACAAAT TACGATCCGT CGTATTTATA GGCGAAAGCA    5040

ATAAACAAAT TATTCTAATT CGGAAATCTT TATTTCGACG TGTCTACATT CACGTCCAAA    5100

TGGGGGCTTA GATGAGAAAC TTCACGATCG ATGCCTTGAT TTCGCCATTC CCAGATACCC    5160

ATTTCATCTT CAGATTGGTC TGAGATTATG CGAAAATATA CACTCATATA CATAAATACT    5220

GACAGTTTGA GCTACCAATT CAGTGTAGCC CATTACCTCA CATAATTCAC TCAAATGCTA    5280

GGCAGTCTGT CAACTCGGCG TCAATTTGTC GGCCACTATA CGATAGTTGC GCAAATTTTC    5340

AAAGTCCTGG CCTAACATCA CACCTCTGTC GGCGGCGGGT CCCATTTGTG ATAAATCCAC    5400

CCATCGGATC TGAATTCTCA CTCATTAGGC NCCCCAGGCT TTACACTTTA TGCTTCCGGC    5460

TCGTATAATG TGTGGAATTG TGAGCGGATA ACAATTTCAC ACAGGAAACA GGATCATGAG    5520

CGGAGAATTA AGGGAGTCAC GTTATGACCC CCGCCGATGA CGCGGGACAA GCCGTTTTAC    5580

GTTTGGAACT GACAGAACCG CAACGATTGA AGGAGCCACT CAGCCGCGGG TTTCTGGAGT    5640

TTAATGAGCT AAGCACATAC GTCAGAAACC ATTATTGCGC GTTCAAAAGT CGCCTAAGGT    5700

CACTATCAGC TAGCAAATAT TTCTTGTCAA AAATGCTCCA CTGACGTTCC ATAAATTCCC    5760

CTCGGTATCC AATTAGAGTC TCATATTCAC TCTCAATCCA AATAATCTGG ATCATGAGCG    5820

GAGAATTAAG GGAGTCACGT TATGACCCCC GCCGATGACG CGGGACAAGC CGTTTTACGT    5880

TTGGAACTGA CAGAACCGCA ACGATTGAAG GAGCCACTCA GCCGCGGGTT TCTGGAGTTT    5940

AATGAGCTAA GCACATACGT CAGAAACCAT TATTGCGCGT TCAAAAGTCG CCTAAGGTCA    6000

CTATCAGCTA GCAAATATTT CTTGTCAAAA ATGCTCCACT GACGTTCCAT AAATTCCCCT    6060

CGGTATCCAA TTAGAGTCTC ATATTCACTC TCAATCCAAA TAATCTGGAT CTGATCAAGA    6120

GACAGGATGA GGATCGTTTC GCATGATTGA ACAAGATGGA TTGCACGCAG GTTCTCCGGC    6180

CGCTTGGGTG GAGAGGCTAT TCGGCTATGA CTGGGCACAA CAGACAATCG GCTGCTCTGA    6240
```

-continued

```
TGCCGCCGTG TTCCGGCTGT CAGCGCAGGG GCGCCCGGTT CTTTTTGTCA AGACCGACCT    6300

GTCCGGTGCC CTGAATGAAC TGCAGGACGA GGCAGCGCGG CTATCGTGGC TGGCCACGAC    6360

GGGCGTTCCT TGCGCAGCTG TGCTCGACGT TGTCACTGAA GCGGGAAGGG ACTGGCTGCT    6420

ATTGGGCGAA GTGCCGGGGC AGGATCTCCT GTCATCTCAC CTTGCTCCTG CCGAGAAAGT    6480

ATCCATCATG GCTGATGCAA TGCGGCGGCT GCATACGCTT GATCCGGCTA CCTGCCCATT    6540

CGACCACCAA GCGAAACATC GCATCGAGCG AGCACGTACT CGGATGGAAG CCGGTCTTGT    6600

CGATCAGGAT GATCTGGACG AAGAGCATCA GGGGCTCGCG CCAGCCGAAC TGTTCGCCAG    6660

GCTCAAGGCG CGCATGCCCG ACGGCGAGGA TCTCGTCGTG ACCCATGGCG ATGCCTGCTT    6720

GCCGAATATC ATGGTGGAAA ATGGCCGCTT TTCTGGATTC ATCGACTGTG GCCGGCTGGG    6780

TGTGGCGGAC CGCTATCAGG ACATAGCGTT GGCTACCCGT GATATTGCTG AAGAGCTTGG    6840

CGGCGAATGG GCTGACCGCT TCCTCGTGCT TTACGGTATC GCCGCTCCCG ATTCGCAGCG    6900

CATCGCCTTC TATCGCCTTC TTGACGAGTT CTTCTGAGCG GGACTCTGGG GTTCGAAATG    6960

ACCGACCAAG CGACGCCCAA CCTGCCATCA CGAGATTTCG ATTCCACCGC CGCCTTCTAT    7020

GAAAGGTTGG GCTTCGGAAT CGTTTTCCGG GACGCCGGCT GGATGATCCT CCAGCGCGGG    7080

GATCTCATGC TGGAGTTCTT CGCCCACCCC CTGCTTTAAT GAGATATGCG AGACGCCTAT    7140

GATCGCATGA TATTTGCTTT CAATTCTGTT GTGCACGTTG TAAAAAACCT GAGCATGTGT    7200

AGCTCAGATC CTTACCGCCG GTTTCGGTTC ATTCTAATGA ATATATCACC CGTTACTATC    7260

GTATTTTTAT GAATAATATT CTCCGTTCAA TTTACTGATT GTACCCTACT ACTTATATGT    7320

ACAATATTAA AATGAAAACA ATATATTGTG CTGAATAGGT TTATAGCGAC ATCTATGATA    7380

GAGCGCCACA ATAACAAACA ATTGCGTTTT ATTATTACAA ATCCAATTTT AAAAAAAGCG    7440

GCAGAACCGG TCAAACCTAA AAGACTGATT ACATAAATCT TATTCAAATT TCAAAAGGCC    7500

CCAGGGGCTA GTATCTACGA CACACCGAGC GGCGAACTAA TAACGTTCAC TGAAGGGAAC    7560

TCCGGTTCCC CGCCGGCGCG CATGGGTGAG ATTCCTTGAA GTTGAGTATT GGCCGTCCGC    7620

TCTACCGAAA GTTACGGGCA CCATTCAACC CGGTCCAGCA CGGCGGCCGG GTAACAGCGG    7680

CCGCTGCCCA ATACGCAAAC CGCCTCTCCC CGCGCGTTGG CCGATTCATT AATGCAGCTG    7740

GCACGACAGG TTTCCCGACT GGAAAGCGGG CAGTGAGCGC AACGCAATTA ATGTGAGTTA    7800

GCTCACTCAT TAGGCACCCC AGGCTTTACA CTTTATGCTT CCGGCTCGTA TGTTGTGTGG    7860

AATTGTGAGC GGATAACAAT TTCACACAGG AAACAGCTAT GACCATGATT ACGAATTCGA    7920

GCTCGGTACC CGGGATCTCC TTTGCCCCGG AGATTACAAT GGACGATTTC CTCTATCTTT    7980

ACGATCTAGG AAGGAAGTTC GAAGGTGAAG GTGACGACAC TATGTTCACC ACTGATAATG    8040

AGAAGGTTAG CCTCTTCAAT TTCAGAAAGA ATGCTGACCC ACAGATGGTT AGAGAGGCCT    8100

ACGCAGCAGG TCTCATCAAG ACGATCTACC CGAGTAACAA TCTCCAGGAG ATCAAATACC    8160

TTCCCAAGAA GGTTAAAGAT GCAGTCAAAA GATTCAGGAC TAATTGCATC AAGAACACAG    8220

AGAAAGACAT ATTTCTCAAG ATCAGAAGTA CTATTCCAGT ATGGACGATT CAAGGCTTGC    8280

TTCATAAACC AAGGCAAGTA ATAGAGATTG GAGTCTCTAA AAAGGTAGTT CCTACTGAAT    8340

CTAAGGCCAT GCATGGAGTC TAAGATTCAA ATCGAGGATC TAACAGAACT CGCCGTGAAG    8400

ACTGGCGAAC AGTTCATACA GAGTCTTTTA CGACTCAATG ACAAGAAGAA AATCTTCGTC    8460

AACATGGTGG AGCACGACAC TCTGGTCTAC TCCAAAAATG TCAAAGATAC AGTCTCAGAA    8520

GACCAAAGGG CTATTGAGAC TTTTCAACAA GGATAATTTC GGGAAACCT CCTCGGATTC    8580

CATTGCCCAG CTATCTGTCA CTTCATCGAA AGGACAGTAG AAAAGGAAGG TGGCTCCTAC    8640
```

```
AAATGCCATC ATTGCGATAA AGGAAAGGCT ATCATTCAAG ATGCCTCTGC CGACAGTGGT   8700

CCCAAAGATG GACCCCCACC CACGAGGAGC ATCGTGGAAA AGAAGACGT  TCCAACCACG   8760

TCTTCAAAGC AAGTGGATTG ATGTGACATC TCCACTGACG TAAGGGATGA CGCACAATCC   8820

CACTATCCTT CGCAAGACCC TTCCTCTATA TAAGGAAGTT CATTTCATTT GGAGAGGACA   8880

CGCTCGAGCT CATTTCTCTA TTACTTCAGC CATAACAAAA GAACTCTTTT CTCTTCTTAT   8940

TAAACCATGG GTTTAGCAGA AAATCAGCTT TGTTTAGACT TGATAGAAGA TTGGATTAAG   9000

AGAAACCCAA AAGGTTCAAT TTGTTCTGAA GGAATCAAAT CATTCAAGGC CATTGCCAAC   9060

TTTCAAGATT ATCATGGCTT GCCTGAATTC AGAAAAGCGA TTGCGAAATT TATGGAGAAA   9120

ACAAGAGGAG GAAGAGTTAG ATTTGATCCA GAAAGAGTTG TTATGGCTGG TGGTGCCACT   9180

GGAGCTAATG AGACAATTAT ATTTTGTTTG GCTGATCCTG GCGATGCATT TTTAGTACCT   9240

TCACCATACT ACCCAGCATT TAACAGAGAT TTAAGATGGA GAACTGGAGT ACAACTTATT   9300

CCAATTCACT GTGAGAGCTC CAATAATTTC AAAATTACTT CAAAAGCAGT AAAAGAAGCA   9360

TATGAAAATG CACAAAAATC AAACATCAAA GTAAAAGGTT TGATTTTGAC CAATCCATCA   9420

AATCCATTGG GCACCACTTT GGACAAAGAC ACACTGAAAA GTGTCTTGAG TTTCACCAAC   9480

CAACACAACA TCCACCTTGT TTGTGACGAA ATCTACGCAG CCACTGTCTT TGACACGCCT   9540

CAATTCGTCA GTATAGCTGA AATCCTCGAT GAACAGGAAA TGACTTACTG CAACAAAGAT   9600

TTAGTTCACA TCGTCTACAG TCTTTCAAAA GACATGGGGT TACCAGGATT TAGAGTCGGA   9660

ATCATATATT CTTTTAACGA CGATGTCGTT AATTGTGCTA GAAAAATGTC GAGTTTCGGT   9720

TTAGTATCTA CACAAACGCA ATATTTTTTA GCGGCAATGC CATCGGACGA AAAATTCGTC   9780

GATAATTTTC TAAGAGAAAG CGCGATGAGG TTAGGTAAAA GGCACAAACA TTTTACTAAT   9840

GGACTTGAAG TAGTGGGAAT TAAATGCTTG AAAAATAATG CGGGGCTTTT TTGTTGGATG   9900

GATTTGCGTC CACTTTTAAG GGAATCGACT TTCGATAGCG AAATGTCGTT ATGGAGAGTT   9960

ATTATAAACG ATGTTAAGCT TAACGTCTCG CTTGGATCTT CGTTTGAATG TCAAGAGCCA  10020

GGTTGGTTTC GAGTTTGTTT CTAGAGTCAA GGGGCAGATC GTTCAAACAT TTGGCAATAA  10080

AGTTTCTTAA GATTGAATCC TGTTGCCGGT CTTGCGATGA TTATCATATA ATTTCTGTTG  10140

AATTACGTTA AGCATGTAAT AATTAACATG TAATGCATGA CGTTATTTAT GAGATGGGTT  10200

TTTATGATTA GAGTCCCGCA ATTATACATT TAATACGCGA TAGAAAACAA AATATAGCGC  10260

GCAAACTAGG ATAAATTATC GCGCGCGGTG TCATCTATGT TACTAGATCG ACCTGCAGGC  10320

ATGCAAGCTT GGCACTGGCC GTCGTTTTAC AACGTCGTGA CTGGGAAAAC CCTGGCGTTA  10380

CCCAACTTAA TCGCCTTGCA GCACATCCCC CTTTCGCCAG CTGGCGTAAT AGCGAAGAGG  10440

CCCGCACCGA TCGCCCTTCC CAACAGTTGC GCAGCCTGAA TGGCGAATGG CGCCAGATCC  10500

CTGAAAGCGA CGTTGGATGT TAACATCTAC AAATTGCCTT TTCTTATCGA CCATGTACGT  10560

AAGCGCTTAC GTTTTTGGTG GACCCTTGAG GAAACTGGTA GCTGTTGTGG GCCTGTGGTC  10620

TCAAGATGGA TCATTAATTT CCACCTTCAC CTACGATGGG GGGCATCGCA CCGGTGAGTA  10680

ATATTGTACG GCTAAGAGCG AATTTGGCCT GTAGACCTCA ATTGCGAGCT TTCTAATTTC  10740

AAACTATTCG GGCCTAACTT TTGGTGTGAT GATGCTGACT GGCAGGATAT ATACCGTTGT  10800

AATCGCTCTT AGCCGTACAA TATTACTCAC CGGTGCGATG CCCCCCATCG TAGGTGAAGG  10860

TGGAAATTAA TGATCCATCT TGAGACCACA GGCCCACAAC AGCTACCAGT TCCTCAAGG   10920

GTCCACCAAA AACGTAAGCG CTTACGTACA TGGTCGATAA GAAAAGGCAA TTTGTAGATG  10980

TTAACATCCA ACGTCGCTTT CAGGGATCTG GCGCCATTCG CCATTCAGGC TGCGCAACTG  11040
```

```
TTGGGAAGGG CGATCGGTGC GGGCCTCTTC GCTATTACGC CAGCTGGCGA AAGGGGGATG   11100

TGCTGCAAGG CGATTAAGTT GGGTAACGCC AGGGTTTTCC CAGTCACGAC GTTGTAAAAC   11160

GACGGCCAGT GCCAAGCTTG CATGCCTGCA GGTCGATCTA GTAACATAGA TGACACCGCG   11220

CGCGATAATT TATCCTAGTT TGCGCGCTAT ATTTTGTTTT CTATCGCGTA TTAAATGTAT   11280

AATTGCGGGA CTCTAATCAT AAAAACCCAT CTCATAAATA ACGTCATGCA TTACATGTTA   11340

ATTATTACAT GCTTAACGTA ATTCAACAGA AATTATATGA TAATCATCGC AAGACCGGCA   11400

ACAGGATTCA ATCTTAAGAA ACTTTATTGC CAAATGTTTG AACCATCTGC CCCTTGACTC   11460

TAGAAACAAA CTCGAAACCA ACCTGGCTCT TGACATTCAA ACGAAGATCC AAGCGAGACG   11520

TTAAGCTTAA CATCGTTTAT AATAACTCTC CATAACGACA TTTCGCTATC GAAAGTCGAT   11580

TCCCTTAAAA GTGGACGCAA ATCCATCCAA CAAAAAAGCC CCGCATTATT TTTCAAGCAT   11640

TTAATTCCCA CTACTTCAAG TCCATTAGTA AAATGTTTGT GCCTTTTACC TAACCTCATC   11700

GCGCTTTCTC TTAGAAAATT ATCGACGAAT TTTTCGTCCG ATGGCATTGC CGCTAAAAAA   11760

TATTGCGTTT GTGTAGATAC TAAACCGAAA CTCGACATTT TTCTAGCACA ATTAACGACA   11820

TCGTCGTTAA AAGAATATAT GATTCCGACT CTAAATCCTG GTAACCCCAT GTCTTTTGAA   11880

AGACTGTAGA CGATGTGAAC TAAATCTTTG TTGCAGTAAG TCATTTCCTG TTCATCGAGG   11940

ATTTCAGCTA TACTGACGAA TTGAGGCGTG TCAAAGACAG TGGCTGCGTA GATTTCGTCA   12000

CAAACAAGGT GGATGTTGTG TTGGTTGGTG AAACTCAAGA CACTTTTCAG TGTGTCTTTG   12060

TCCAAAGTGG TGCCCAATGG ATTTGATGGA TTGGTCAAAA TCAAACCTTT TACTTTGATG   12120

TTTGATTTTT GTGCATTTTC ATATGCTTCT TTTACTGCTT TTGAAGTAAT TTTGAAATTA   12180

TTGGAGCTCT CACAGTGAAT TGGAATAAGT TGTACTCCAG TTCTCCATCT TAAATCTCTG   12240

TTAAATGCTG GGTAGTATGG TGAAGGTACT AAAAATGCAT CGCCAGGATC AGCCAAACAA   12300

AATATAATTG TCTCATTAGC TCCAGTGGCA CCACCAGCCA TAACAACTCT TTCTGGATCA   12360

AATCTAACTC TTCCTCCTCT TGTTTTCTCC ATAAATTTCG CAATCGCTTT TCTGAATTCA   12420

GGCAAGCCAT GATAATCTTG AAAGTTGGCA ATGGCCTTGA ATGATTTGAT TCCTTCAGAA   12480

CAAATTGAAC CTTTTGGGTT TCTCTTAATC CAATCTTCTA TCAAGTCTAA ACAAAGCTGA   12540

TTTTCTGCTA AACCCATGGT TTAATAAGAA GAGAAAAGAG TTCTTTTGTT ATGGCTGAAG   12600

TAATAGAGAA ATGAGCTCGA GCGTGTCCTC TCCAAATGAA ATGAACTTCC TTATATAGAG   12660

GAAGGGTCTT GCGAAGGATA GTGGGATTGT GCGTCATCCC TTACGTCAGT GGAGATGTCA   12720

CATCAATCCA CTTGCTTTGA AGACGTGGTT GGAACGTCTT CTTTTTCCAC GATGCTCCTC   12780

GTGGGTGGGG GTCCATCTTT GGGACCACTG TCGGCAGAGG CATCTTGAAT GATAGCCTTT   12840

CCTTTATCGC AATGATGGCA TTTGTAGGAG CCACCTTCCT TTTCTACTGT CCTTTCGATG   12900

AAGTGACAGA TAGCTGGGCA ATGGAATCCG AGGAGGTTTC CCGAAATTAT CCTTTGTTGA   12960

AAAGTCTCAA TAGCCCTTTG GTCTTCTGAG ACTGTATCTT TGACATTTTT GGAGTAGACC   13020

AGAGTGTCGT GCTCCACCAT GTTGACGAAG ATTTTCTTCT TGTCATTGAG TCGTAAAAGA   13080

CTCTGTATGA ACTGTTCGCC AGTCTTCACG GCGAGTTCTG TTAGATCCTC GATTTGAATC   13140

TTAGACTCCA TGCATGGCCT TAGATTCAGT AGGAACTACC TTTTTAGAGA CTCCAATCTC   13200

TATTACTTGC CTTGGTTTAT GAAGCAAGCC TTGAATCGTC CATACTGGAA TAGTACTTCT   13260

GATCTTGAGA AATATGTCTT TCTCTGTGTT CTTGATGCAA TTAGTCCTGA ATCTTTTGAC   13320

TGCATCTTTA ACCTTCTTGG GAAGGTATTT GATCTCCTGG AGATTGTTAC TCGGGTAGAT   13380

CGTCTTGATG AGACCTGCTG CGTAGGCCTC TCTAACCATC TGTGGGTCAG CATTCTTTCT   13440
```

```
GAAATTGAAG AGGCTAACCT TCTCATTATC AGTGGTGAAC ATAGTGTCGT CACCTTCACC    13500

TTCGAACTTC CTTCCTAGAT CGTAAAGATA GAGGAAATCG TCCATTGTAA TCTCCGGGGC    13560

AAAGGAGATC CCGGGTACCG AGCTCGAATT CGTAATCATG GTCATAGCTG TTTCCTGTGT    13620

GAAATTGTTA TCCGCTCACA ATTCCACACA ACATACGAGC CGGAAGCATA AAGTGTAAAG    13680

CCTGGGGTGC CTAATGAGTG AGCTAACTCA CATTAATTGC GTTGCGCTCA CTGCCCGCTT    13740

TCCAGTCGGG AAACCTGTCG TGCCAGCTGC ATTAATGAAT CGGCCAACGC GCGGGGAGAG    13800

GCGGTTTGCG TATTGGGCAG CGGCCGCTGT TACCCGGCCG CCGTGCTGGA CCGGGTTGAA    13860

TGGTGCCCGT AACTTTCGGT AGAGCGGACG GCCAATACTC AACTTCAAGG AATCTCACCC    13920

ATGCGCGCCG GCGGGGAACC GGAGTTCCCT TCAGTGAACG TTATTAGTTC GCCGCTCGGT    13980

GTGTCGTAGA TACTAGCCCC TGGGGCCTTT TGAAATTTGA ATAAGATTTA TGTAATCAGT    14040

CTTTTAGGTT TGACCGGTTC TGCCGCTTTT TTTAAAATTG GATTTGTAAT AATAAAACGC    14100

AATTGTTTGT TATTGTGGCG CTCTATCATA GATGTCGCTA TAAACCTATT CAGCACAATA    14160

TATTGTTTTC ATTTTAATAT TGTACATATA AGTAGTAGGG TACAATCAGT AAATTGAACG    14220

GAGAATATTA TTCATAAAAA TACGATAGTA ACGGGTGATA TATTCATTAG AATGAACCGA    14280

AACCGGCGGT AAGGATCTGA GCTACACATG CTCAGGTTTT TTACAACGTG CACAACAGAA    14340

TTGAAAGCAA ATATCATGCG ATCATAGGCG TCTCGCATAT CTCATTAAAG CAGGGGGTGG    14400

GCGAAGAACT CCAGCATGAG ATCCCCGCGC TGGAGGATCA TCCAGCCGGC GTCCCGGAAA    14460

ACGATTCCGA AGCCCAACCT TTCATAGAAG GCGGCGGTGG AATCGAAATC TCGTGATGGC    14520

AGGTTGGGCG TCGCTTGGTC GGTCATTTCG AACCCCAGAG TCCCGCTCAG AAGAACTCGT    14580

CAAGAAGGCG ATAGAAGGCG ATGCGCTGCG AATCGGGAGC GGCGATACCG TAAAGCACGA    14640

GGAAGCGGTC AGCCCATTCG CCGCCAAGCT CTTCAGCAAT ATCACGGGTA GCCAACGCTA    14700

TGTCCTGATA GCGGTCCGCC ACACCCAGCC GGCCACAGTC GATGAATCCA GAAAAGCGGC    14760

CATTTTCCAC CATGATATTC GGCAAGCAGG CATCGCCATG GGTCACGACG AGATCCTCGC    14820

CGTCGGGCAT GCGCGCCTTG AGCCTGGCGA ACAGTTCGGC TGGCGCGAGC CCCTGATGCT    14880

CTTCGTCCAG ATCATCCTGA TCGACAAGAC CGGCTTCCAT CCGAGTACGT GCTCGCTCGA    14940

TGCGATGTTT CGCTTGGTGG TCGAATGGGC AGGTAGCCGG ATCAAGCGTA TGCAGCCGCC    15000

GCATTGCATC AGCCATGATG GATACTTTCT CGGCAGGAGC AAGGTGAGAT GACAGGAGAT    15060

CCTGCCCCGG CACTTCGCCC AATAGCAGCC AGTCCCTTCC CGCTTCAGTG ACAACGTCGA    15120

GCACAGCTGC GCAAGGAACG CCCGTCGTGG CCAGCCACGA TAGCCGCGCT GCCTCGTCCT    15180

GCAGTTCATT CAGGGCACCG GACAGGTCGG TCTTGACAAA AAGAACCGGG CGCCCTGCG    15240

CTGACAGCCG GAACACGGCG GCATCAGAGC AGCCGATTGT CTGTTGTGCC CAGTCATAGC    15300

CGAATAGCCT CTCCACCCAA GCGGCCGGAG AACCTGCGTG CAATCCATCT TGTTCAATCA    15360

TGCGAAACGA TCCTCATCCT GTCTCTTGAT CAGATCC                             15397
```

DELAYED RIPENING TOMATO PLANTS WITH T-DNA BEARING A TRUNCATED ACC2 SYNTHASE GENE

This application claims the benefit of U.S. Provisional Application No. 60/000,721, filed Jun. 30, 1995.

BACKGROUND OF THE INVENTION

The present invention relates generally to the breeding of tomato plants. More specifically, the invention relates to the introduction of a transgene that confers a delayed ripening phenotype on tomato plants.

The plant hormone ethylene has a profound influence on plant physiology. Active in trace amounts, it affects a number of processes such as fruit ripening, seed germination, plant growth, leaf and flower senescence, pathogen infection, and the interaction of plants with their environment. In particular, ethylene induces a number of physiological changes associated with fruit ripening such as accumulation of carotenoid pigments, conversion of cholorplasts to chromoplasts, the increased expression of genes encoding cell wall degradation enzymes, fruit softening and susceptibility to pathogens.

Control of the effects of ethylene is a particularly useful approach to controlling fruit ripening in tomato. More than 80% of tomatoes (by volume) currently sold in the United States are picked while green. Growers harvest green tomatoes for several reasons: (1) green tomatoes are firmer, enabling them to withstand shipping and handling with less injury; (2) a green tomato harvest is less labor-intensive and less costly than a vine-ripe harvest and (3) green fruit stays in the field for a shorter period of time reducing the risk of loss from weather or pests.

After harvest, either the packer or the repacker exposes the green tomatoes to an external source of ethylene gas to cause the tomatoes to develop red color. This practice reddens the fruit, but these tomatoes will not always develop full flavor when picked at the green stage. Fruit that have begun to ripen need to be shipped at a low temperature to delay ripening, however these low temperatures decrease fruit quality. Frequently, a portion of the green fruit is harvested at the immature green stage, which means that it will never achieve full ripeness even with the application of ethylene. Such tomatoes, together with other distribution-damaged tomatoes, do not achieve full flavor potential and, we believe, are a major factor contributing to consumer dissatisfaction with current fresh market tomatoes.

In tomato (and other so called climacteric fruit), fruit ripening is associated with a burst of respiration and a concomitant increase in ethylene production. Once ripening is initiated, the endogenous ethylene production rises autocatalytically.

If ethylene production could be controlled, tomato fruit could be left on the vine longer to develop the fruit components which contribute to flavor. The present invention addresses these and other needs.

SUMMARY OF THE INVENTION

The present invention provides tomato plants comprising a genetic locus having a sequence substantially identical to (SEQ ID No: 1). The plants bear fruit that display significant ripening impairment once the breaker stage is reached. In particular, the fruit reach pink stage about 2 to about 3 weeks after breaker stage, when the fruit are picked at breaker stage and stored at 15° C. Preferred plants are germinated from seed deposited with the American Type Culture Collection under Accession No. 97305.

The invention further provides tomato fruit from the plants of the invention. The fruit of the invention have ethylene levels less than about 1.0 nl/g/hr, preferably less than about 0.5 nl/g/hr.

The invention also provides methods of tomato plants with decreased ethylene production. The methods comprise crossing a parent tomato plant with a tomato plant comprising a genetic locus of the invention. The tomato plant comprising the genetic locus can be a plant germinated from seed deposited with American Type Culture Collection under Accession No. 97305. The method may further comprise the step of selecting progeny bearing fruit that reach pink stage about 2 to about 3 weeks after breaker stage, when the fruit are picked at breaker stage and stored at 15° C.

Definitions

The phrase "nucleic acid sequence" refers to a single or double-stranded polymer of deoxyribonucleotide or ribonucleotide bases read from the 5' to the 3' end. It includes both self-replicating plasmids, infectious polymers of DNA or RNA and non-functional DNA or RNA.

The term "tomato plant" includes whole tomato plants, tomato plant organs (e.g., leaves, stems, roots, etc.), seeds and tomato plant cells and progeny of same.

A tomato plant is "derived from" seed or another plant, if it is germinated directly from the seed or is progeny of the plant or seed (e.g., $F_1$, $F_2$, etc.) as a result of standard sexual reproduction.

A "primary transformant" is a plant regenerated from one or more plant cells transformed in vitro with a recombinant DNA construct.

A "heterologous sequence" is one that originates from a foreign species, or, if from the same species, is substantially modified from its original form. For example, a heterologous promoter operably linked to structural gene is from a species different from that from which the structural gene was derived, or, if from the same species, is different from the promoter normally present with the gene, or is substantially modified from its original form.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444

(1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection. These references are incorporated herein by reference.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

DESCRIPTION OF THE PREFERRED EMBODIMENTS

Figure 1:
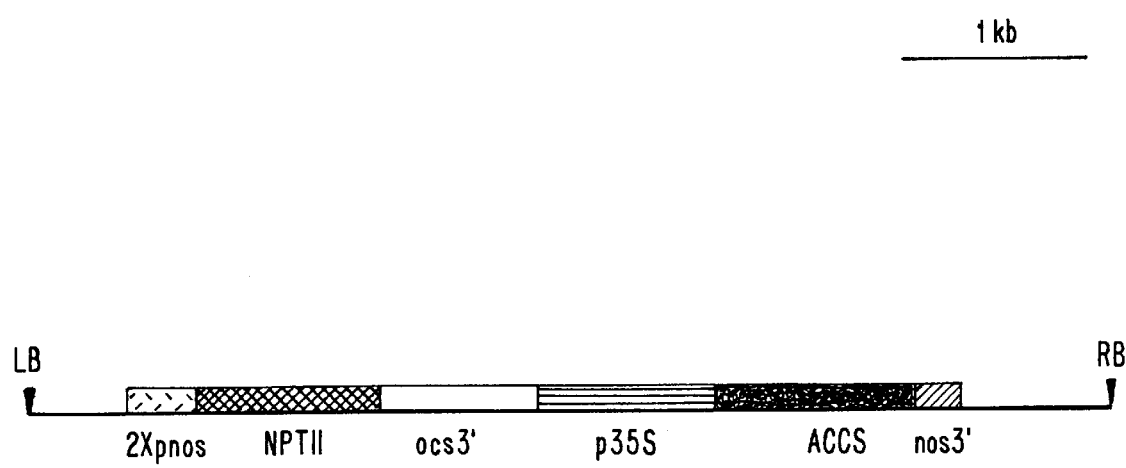
FIG. 1 is a schematic diagram of the T-DNA region of pWTT2 144/AccS.

The present invention provides tomato plants (*Lycopersicon esculentum*) comprising a stably incorporated locus that confers a delayed fruit ripening phenotype on the plant. In particular, the tomato plants of the invention contain a T-DNA insert comprising a sequence (the AccS transgene) derived from a tomato fruit-specific aminocyclopropane carboxylate (ACC) synthase gene, but that does not encode a functional ACC synthase enzyme.

ACC synthase is the rate limiting enzyme that converts s-adenosylmethionine to 1-aminocyclopropane-1-carboxylic acid, the immediate precursor to ethylene. As explained in detail below, incorporation of the AccS transgene in a tomato plant genome inhibits expression of the ACC synthase gene. Inhibition of ACC synthase biosynthesis results in reduced levels of ethylene biosynthesis. Thus, fruit of tomato plants comprising the transgene exhibit a delayed ripening phenotype, but ripen normally when external ethylene is applied.

As used herein an "AccS transgene" is a truncated coding region from the tomato Acc2 gene which is fused to a 35S promoter from cauliflower mosaic virus and a nos3' termination sequence from *Agrobacterium tumefaciens*. In particular, the sequence from the Acc2 gene is a sequence consisting of nucleotide 149 to nucleotide 1237. Rottman et al. *J. Mol. Biol.* 222:937–961 (1991).

The plants of the invention are derived, directly or indirectly, from transformation of a tomato plant cell with a construct comprising a T-DNA having the following regions: (1) LB, the left border region of Agrobacterium T-DNA; (2) 2χpnos, a tandem duplicate untranslated promoter region of the nopaline synthase gene from Agrobacterium; (3) nptII, the neomycin phosphotransferase gene from Tn5; (4) ocs3', the 3' untranslated genion of the octopine synthase gene from Agrobacterium; (5) LacZ', an untranslated LacZ polylinker sequence; (6) p35S, the 35S promoter form cauliflower mosaic virus (7) Cab22L, the leader sequence corresponding to the 5' untranslated region of the Cab22R gene from petunia fused to the 35S promoter; (8) AccS, the truncated coding region from base 149 to base 1237 of the tomato Acc2 gene; (9) nos 3', the untranslated 3' region of the nopaline synthase gene from Agrobacterium; and (10) RB, a right border region of Agrobacterium T-DNA.

The "T-DNA insert" of the invention comprises three copies of the T-DNA described above. The three copies are arranged in inverted repeats at the LB and RB. At the LB-LB and RB-RB junction, one border is deleted such that there is only one complete border at each junction. The LB and RB at either end of the T-DNA structure are also deleted.

An exemplary plasmid comprising the T-DNA described above, pWTT2144/AccS, is described in detail below. This plasmid is used to generate transgenic tomato plants using *Agrobacterium tumefaciens*-mediated transformation techniques. Stable insertion of the AccS transgene into the tomato genome in the sense orientation can result in downregulation of expression of the corresponding endogenous Acc2 gene and a reduction in ethylene biosynthesis in the ripening fruit. The technique is an example of Transwitch™ suppression (U.S. Pat. No. 5,283,184). One feature of Transwitch™ gene suppression is the reduced accumulation of the targeted gene mRNA (reduced steady state RNA). The trait (level of suppression), once selected through the first sexual generation, behaves in a simple Mendelian fashion.

The methods of the present invention can be used to delay fruit ripening of any tomato (large fruited or cherry) cultivar for fresh market or processing tomato production. Exemplary cultivars that can be used include essentially all commercial cultivars. For listings of suitable tomatoes see, Rick, in *Evolution of Crop Plants* N. W. Simmonds, ed.

pp268–273 (Longman, London, 1976) and Taylor in *The Tomato Crop* pp1–35 (Chapman and Hall, London, 1986).

A tomato plant of the present invention can be obtained by crossing a plant comprising the T-DNA insert of the invention with any tomato cultivar lacking the insert. Any standard method used for crossing tomato plants can be used to introduce the transgene into the genome of the desired plant. Generally, the methods involve emasculation of one parent, followed by application of pollen from the other parent to the stigma of the first parent. The crosses can be performed using either parent as the pollen parent. Embryo rescue can also be performed if the flowers abort after pollination.

The plant containing the T-DNA insert can be a plant derived from primary transformants or can be a plant in which the factor was introduced through a sexual cross. Preferred plants of the invention are those derived from seed deposited with the American Type Culture Collection (ATCC) Accession No. 97305.

A number of methods can be used to determine if a tomato plant exhibiting a delayed ripening phenotype comprises the T-DNA insert of the invention in its genome. The terms used herein to describe ripeness of tomato fruit are according to standard ripeness classes as described, for instance, in *The Tomato Crop* Atherton and Rudich eds. (Chapman Hall, 1986). The ripeness classes for a given given fruit are set forth in Table 1.

TABLE 1

| Score | Class | Description |
|---|---|---|
| 1 | Green | Entirely light to dark-green, but mature. |
| 2 | Breaker | First appearance of external pink, red or tannish-yellow color, not more than 10%. |
| 3 | Turning | Over 10%, but not more than 30% red, pink or tannish-yellow. |
| 4 | Pink | Over 30%, but not more than 60% pinkish or red. |
| 5 | Light red | Over 60%, but not more than 90% red. |
| 6 | Red | Over 90% red, desirable table ripeness. |

Fruit of the plants of the invention reach breaker stage between about 40 and about 70 days after anthesis, usually between about 45 and about 60 days after anthesis. The fruit, however, differ significantly from wild type fruit in terms of ripening inhibition. On the vine, the fruit of plants of the invention typically remain at the breaker stage 5 to 7 days longer than wild type. The transition from breaker stage to light red stage in the ripening impaired fruit is further delayed with respect to the transition for wild type fruit. Under field conditions the fruit of the invention typically require approximately 21 days to proceed from the breaker stage to light red stage, whereas wild type fruit typically require 4 to 5 days to turn from the breaker stage to the red stage. The ripening impaired fruit under field conditions can remain indefinitely at the light red stage without ever reaching the red stage.

There are analogous differences in ripening for off the vine fruit picked at the breaker stage and stored at 15° C. Ripening impaired fruit of the invention typically require at least about 2 weeks (typically about 3 weeks) to reach the pink stage, and while some may reach the light red stage, the fruit can remain indefinitely without reaching the red stage. Fruit will, however, reach the red stage upon the application of ethylene. This is to be contrasted with wild type fruit which typically require 5 to 7 days to reach red ripe stage from the breaker stage under comparable conditions.

Fruit color development, as measured by the a/b ratio measures about 5 to about 10 fold less in the fruit of the invention as compared to control fruit at the breaker or equivalent stage. Standard methods for determining tomato fruit color are described, for instance, in Gull et al. *J. Amer. Soc. Hort. Sci.* 114:950–954 (1989) and Kader et al. *Hort. Sci.* 13:577–578 (1978). At the time the control fruit are red ripe, the levels of color in the fruit of the invention are 4 to 5 times lower.

In addition, the fruit do not synthesize normal levels of ethylene during ripening. Typically, the level which is detected at the breaker or equivalent stage is less than about 0.5 nl/g/hr, usually about 0.1 nl/g/hr as measured using a standard assay as described in Grierson and Tucker, *Planta* 157:174–179 (1983) and Sawamura et al. *Plant Cell Physiol.* 19:1061–1069 (1978). At the pink stage which follows the breaker stage the fruit continue to have ethylene levels which are reduced by about 50 to about 100 fold compared to control fruit.

Since the T-DNA inserts comprise NPTII genes, kanamycin resistance can be determined using selective media or by spraying 10–14 day old tomato seedlings with a solution of kanamycin (1 g/L) on three consecutive days. The levels of Acc2 mRNA can be measured using standard techniques such as Northern blots, RNAse protection assays and the like. To further characterize the plants nucleic hybridization techniques can be used to determine structure of the T-DNA insert in the plant. The example section, below, provides a detailed description of the molecular characterization of the T-DNA insert of the invention.

The precise locus in which the T-DNA insert of the invention is integrated can be determined using standard genetic and molecular mapping techniques well known to those of skill in the art. Obviously, for plants derived either directly or indirectly from a particular plant or seed containing the T-DNA insert (e.g., those deposited with the ATCC under Accession No. 97305), the locus will be the same as the parent plant.

The following example is provided to illustrate, but not limit the claimed invention.

EXAMPLE 1

A. Agrobacterium-Mediated Transformation S ystem

Introduction of DNA into plant tissue by Agrobacterium-mediated transformation as described in U.S. Pat. No. 5,283,184. The vector system used to transfer the AccS transgene into tomato is based on the Ti plasmid from *Agrobacterium tumefaciens*.

The T-DNA plasmid, pWTT2144/AccS, used in these transformations is composed of: (1) the replication of origin from pACYC184 that ensures replication in *Escherichia coli*; (2) the pVS1 replicon (derived from *Pseudomonas aeruginosa* DNA) that ensures replication in *A. tumefaciens*; (3) the tetracycline resistance marker from plasmid RP1 that allows for selection of the binary plasmid in *A. tumefaciens* and *E. coli*, and (4) the left and right border regions of T-DNA from an octopine strain of *A. tumefaciens* which surround the DNA insertion in the plant genome.

Within the T-DNA are the nptII gene from transposon Tn5 that encodes enzyme neomycin phosphotransferase II and serves as a selectable marker for transformed plant cells, fused to a nopaline synthase (nos) promoter sequence and octopine synthase (ocs3') termination sequence from *A. tumefaciens*, and the LacZ' polylinker region with multiple restriction sites for cloning of genes to be transferred. The T-DNA has an insertion of a truncated Acc2 gene coding region fused to the 35S promoter from cauliflower mosaic virus and the nos3' termination sequence in the LacZ' polylinker region of pWTT2144.

Plasmid pWTT2144 was transferred from *E. coli* to *A. tumefaciens* LBA4404, which carries the pAL4404 vir plasmid, by a triparental mating procedure as described by Figurski et al., *Proc. Natl. Acad. Sci. USA* 76:1648–1652 (1979).

The plasmid pWTT2144/AccS was used to transform the parental line 91103-114 to generate line 1345-4, described in detail below. The T-DNA region of this plasmid consists of the following sequences (see, FIG. 1):

CaMV35S. The 35S promoter region is derived from cauliflower mosaic virus and controls expression of the AccS gene. The 35S promoter directs high level constitutive expression and is widely used as a promoter for high expression of transgenes.

Cab22L leader. The Cab22L leader sequence (Cab22L) is a 69 bp fragment of *Petunia hybrida* genomic DNA which was derived from the Cab22L gene and corresponds to the 5' untranslated region for that gene.

AccS. The AccS gene is a truncated coding region derived from an ACC synthase gene (Acc2) isolated from tomato (*L. esculentum*). The AccS gene corresponds to a 1088 bp region of the Acc2 gene from base 149 to base 1237. The AccS gene does not encode a functional ACC synthase enzyme.

Termination sequences. The nopaline synthase (nos3') and octopine synthase (ocs3') gene termination sequences from *A. tumefaciens* function in the expression of the AccS and nptII genes, respectively.

2Xpnos Promoter. The nos promoter is present in line 1345-4 as a duplicate tandem repeat of the untranslated 5' region of the nopaline synthase gene from *A. tumefaciens*. It functions in line 1345-4 in the expression of the nptII selectable marker gene. This sequence, as used in line 1345-4, no longer functions as a regulated article since it is not associated with the nopaline synthase coding region which functions in *A. tumefaciens*.

NptII. The nptII gene is a coding region originally isolated from transposon Tn5. It encodes a protein, neomycin phosphotransferase II, which catalyzes the phosphorylation of certain aminoglycoside antibiotics, rendering transformed cells resistant to kanamycin. It functions in line 1345-4 as a selectable marker.

LacZ' polylinker sequence. The untranslated LacZ' polylinker sequence functions in line 1345-4 as a site for cloning the AccS transgene into the binary vector pWTT2144.

Borders. The left and right border regions of T-DNA from *A. tumefaciens* function in the transfer of gene sequences into the tomato genome. The border regions are the only necessary cis-acting elements in T-DNA for T-DNA insertion. The use of a binary vector system allows for other necessary transfer elements to act in trans so that only the border regions are required to be integrated into the plant host genome. The T-DNA borders are only partially transferred to the tomato genome; during the transformation process, the left border is cut between nucleotides 293 and 294 (left border nick) while the right border is cut between nucleotides 7603 and 7604 (right border nick). This cleavage reduces the length of the right border fragment of pWTT2144/AccS from 1900 bp to 303 bp in the T-DNA and the left border fragment of pWTT2144/AccS from 880 bp to 589 bp in the T-DNA (FIG. 1).

B. Description of Non-transformed Tomato Cultivar 91103-114

DNAP tomato line 91103-114 is a somaclone derived from the breeding line FL7181 developed by Dr. Jay Scott at the University of Florida. Line FL7181 is characterized as a determinate large-fruited variety with an average fruit weight of 8 oz. Fruit are globate to slightly elliptical in shape and are substantially firmer than fruit of comparable varieties (i.e., Floradade). Fruit shoulders are smooth and exhibit a darker green shade than the rest of the fruit surface before ripening. Fruit ripen to a deep crimson red interior color due to the presence of the og$^c$ allele. The fruit stem (pedicel) lacks a joint. This line is known to be resistant to Verticillium wilt race 1 and Fusarium wilt races 1 and 2.

The DNAP line 91103-114 exhibits all of the traits described above, but differs from FL7181 principally by reduced blossom end scar size, strong main stem and increased foliage cover for fruit. Line 91103-114 also differs from FL7181 in its adaptation to diverse growth environments; while FL7181 is specifically adapted to Florida growing regions, 91103-114 has proven to grow well in other regions (e.g., California).

C. Description, History and Mendelian Inheritance of Delayed-Ripening Tomato Line 1345-4

The line 1345-4 is a homozygous $T_2$ selection from an original $T_0$ transformant 1345, obtained after *Agrobacterium tumefaciens* transformation of the DNAP line 91103-114 with binary vector pWTT2144/AccS.

The primary transformant 1345 was selected in a greenhouse screen of several hundred primary transformants to have fruit which did not ripen when left on the vine. Subsequently, 10 of the 1345 $T_1$ seed (derived from self fertilization) which were prescreened for kanamycin resistance were screened in the greenhouse and observations on the plant and fruit phenotype were made. Plant 1345-4 was selected as having fruit which did not ripen on the vine. The 1345-4 plant was shown to be homozygous for the T-DNA locus. Seed from the self-fertilization of 1345-4 have been subsequently analyzed in multiple field trials over multiple growing seasons.

No instability in the delayed-ripening phenotype has been observed in any field trials. Two independent ways have been used to monitor the stability of line 1345-4. First, it is possible to establish that the T-DNA insertion is stable and intact by measuring kanamycin resistance in large populations of seedlings in the greenhouse. It was established that the 1345 plant was carrying a single T-DNA insertion by evaluating the segregation of kanamycin resistance in the primary transformant. Subsequently, multiple kanamycin-resistant T2 plants were selected and segregation of the kanamycin-resistant phenotype in progeny plants arising from self-fertilization of the selected T2 plants was evaluated. The T3 plants from 1345-4 were all kanamycin resistant, hence it was deduced that the 1345-4 plant was homozygous.

The second approach to evaluating the stability of line 1345-4 is through observation of the delayed-ripening phenotype in the field. A number of separate field trials for the evaluation of the homozygous 1345-4 line and progeny derived from it have been carried out. These trials have involved the evaluation of fruit on at least 2000 separate plants of 1345-4. During these evaluations, which involved observations of the individual plants at multiple times during the ripening process and the harvest of fruit from all of the plants, no exceptional plants in which all the fruit ripen at the normal rate have been observed.

D. DNA Analysis of Delayed-Ripening Tomato Line 1345-4

Figure 2:
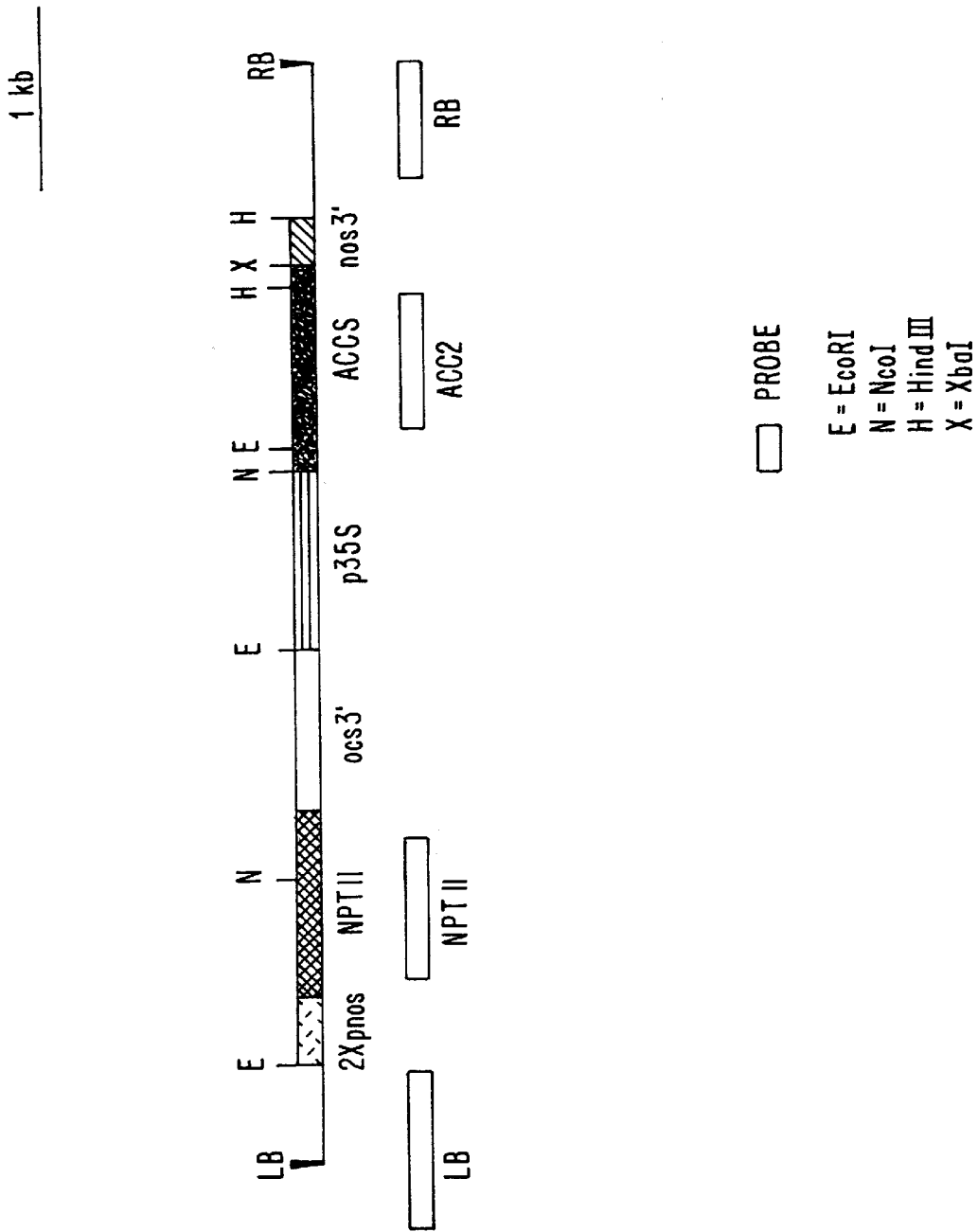
FIG. 2 is a restriction map of the T-DNA region of pWTT2144/AccS showing the location of the hybridization probes used in the genomic mapping.
Figure 3:
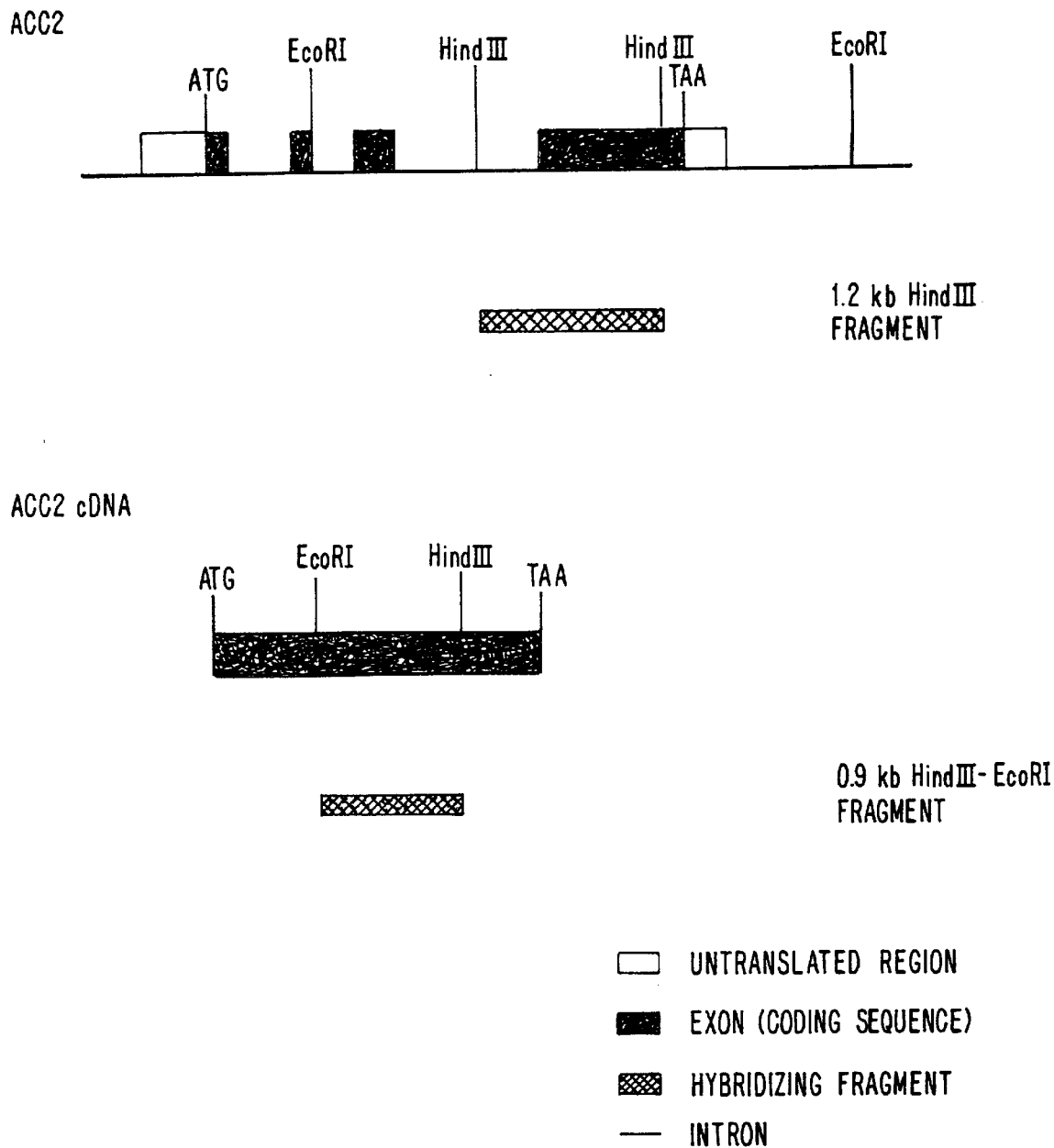
FIG. 3 is a schematic diagram showing the Acc2 genomic region and Acc2 cDNA and the fragments used as probes to determine transgene structure in the 1345-4 transformant.

To determine the nature and number of insertions which have occurred in line 1345, Southern hybridizations were used to characterize the structure of the T-DNA inserts in the genomic DNA, in conjunction with the nptII segregation data described above which indicates the T-DNA locus number. The T-DNA is defined as the region between the left and right borders of the binary vector pWTT2144/AccS that is transferred into the plant (see FIG. 1). This region includes the nptII selectable marker and the truncated ACC synthase gene (AccS), together with the left and right border sequences. FIG. 2 shows the restriction enzymes used to cleave the DNA and the location of the four probes used to determine the structure of T-DNA insert, the left border (LB), nptII, Acc2, and right border (RB) probes.

1. Copy Number

The number of additional AccS genes in 1345 was determined by digesting genomic DNA from transgenic plants with HindIII and EcoRI, then after electrophoresis and transfer to nylon membranes, hybridizing to a $^{32}$P-labeled Acc2 probe. This probe hybridizes to a 0.9 kb EcoRI-HindIII fragment from the transgene (AccS) and a 1.2 kb HindIII fragment from the endogenous Acc2 gene which includes an additional 300 bp of intron sequence. By comparing the intensity of the transgene and endogenous bands, a determination of the number of copies of the transgene can be made in either the hemizygous primary transformant or homozygous S1 progeny. The hybridization patterns of genomic DNA from an untransformed tomato plant, Baxter's Early Bush Cherry (BEB) and 1345-4 digested with HindIII and EcoRI and hybridized to the Acc2 probe were analyzed. In 1345-4, the homozygous S1 progeny of 1345, the endogenous gene to transgene ratio is greater than 2 suggesting that there are at least 2 copies of AccS in the transgenic DNA. Since the nptII gene segregates as a single locus, it is most probable that the 2–3 copies of the T-DNA are present at a single locus.

2. T-DNA Structure

It is known that a single intact copy or multiple T-DNA copies can be inserted at a single locus as direct or inverted repeats around either the left or right border, and it is known that deletions of the T-DNA or insertions of genomic DNA may be present between the T-DNA copies (Jorgenson et al., *Mol. Gen. Genet.* 207:471–477 (1987)). To determine the organization of the T-DNAs in the 1345 genome, we hybridized several different probes to the 1345-4 genome digested with several restriction enzymes. FIG. 2 shows the relative map position of the probes in the T-DNA.

Left and Right Borders: Eco-RI digestions were done to determine the number of intact left and right border fragments. EcoRI sites in the T-DNA are located approximately 500 bp in from the LB and 2.1 kb in from the RB (within the AccS transgene). The fragments hybridizing to the specific border probe will be at least this size. If there is an inverted repeat at the LB and the borders are intact and flush, we would expect to see a 1 kb EcoRI fragment hybridizing only to the LB. For the RB, an intact inverted repeat would give a 4.2 kb fragment that hybridizes to the RB fragment as well as to the AccS probe. A direct LB-RB repeat would result in a fragment of 2.6 kb that hybridizes to both border probes and AccS.

In 1345-4 DNA cut with EcoRI, a 2.9 kb fragment hybridizes to the LB probe only and a 3.5 kb fragment hybridizes to the RB probe only, indicating that there is one intact left and right border. Likewise, the NcoI digestions show single hybridizing bands with both probes and the fragments are of appropriate sizes (LB fragment, greater than 1.6 kb and RB fragment greater than 2.3 kb). The HindIII and XbaI digests also show single bands of appropriate sizes which suggests that there is a single complete T-DNA insertion. However, we know from the copy number blots (see above) that there are at least two copies of the AccS transgene. Together these results suggest that a deleted form of T-DNA, containing an intact AccS gene but missing one or both of the borders, is also present. There are no direct repeat structures since the LB and RB probes do not hybridize to the same fragment. There could, however, be inverted or indirect repeats around either border. Hybridizations with the nptII and AccS probes were done to further characterize the T-DNA insertions.

nptII: If the T-DNA is intact, the nptII probe will hybridize to a single 2.4 kb EcoRI fragment containing the entire 2Xpnos-nptII-ocs3' fusion (see FIG. 2). In 1345-4 genomic DNA cut with EcoRI, the expected 2.4 kb fragment is present in addition to two other hybridizing fragments of 5.2 kb and 2.9 kb. The 2.9 kb fragment also hybridizes to the left border probe which indicates that there is probably one complete internal copy and 2 incomplete copies of T-DNA with deletions occurring at the LB. Since the 2.9 kb EcoRI fragment hybridizes to both nptII and LB probes, this junction is likely an inverted repeat with a deletion of one of the borders that includes the EcoRI site. Hybridization of an EcoRI fragment to both the LB probe and the nptII probe can only occur if a deletion eliminates one of the EcoRI sites.

Since NcoI cleaves within the nptII coding sequence, digestion of the T-DNA with this enzyme will give two nptII fragments, one of 2.1 kb which spans the nptII 3' coding region up to the NcoI site located at the ATG of the AccS transgene, and one of 1.2 kb in length which includes the 5' nptII coding region and LB to the next NcoI site in either genomic DNA or adjacent T-DNA insertion. If there is a perfect inverted repeat at the LB, we expect a 3.3 kb NcoI fragment that hybridizes to both the nptII and LB probes. Based on the results from the EcoRI digestion, we expect the 2.1 kb fragment to be present, as well as two fragments greater than 1.2 kb. One of these will also hybridize to, the LB. As predicted, the 2.1 kb fragment is present as well as a 6.6 kb fragment and a 2.9 kb fragment which also hybridizes to the LB probe. This is consistent with the presence of three T-DNA copies, one which is complete and intact, one which is an inverted repeat with a deletion (approximately 600 bp) extending to the LB, and a second inverted repeat with a deletion (approximately 50 bp) extending to the right border.

AccS: Hybridization with the AccS probe will give fragments greater than 2.3 kb and 2.1 kb for NcoI and EcoRI digests respectively. These fragments will also hybridize to the RB probe if the border is intact. The results show two hybridizing fragments for NcoI, 15 kb and 3.8 kb, and two for EcoRI, 4 kb and 3.5 kb. The 3.8 kb NcoI fragment and the 3.5 kb EcoRI fragment also hybridize to the RB. These results confirm that there are at least 2 copies of AccS, and that one copy is present on a T-DNA with a deleted RB. To demonstrate that AccS itself has not been deleted or rearranged, NcoI/XbaI double digests were done to drop out the intact 1.1 kb fragment containing the complete truncated gene.

Linkage of AccS and nptII: XbaI and HindIII cleave the T-DNA once approximately 1 kb in from the right border. Digestion with either of these enzymes will generate fragments containing both the nptII and AccS genes. After XbaI digestion, a 9.2 kb and a 6.2 kb fragment hybridized with both probes. After HindIII digestion, a 9.2 kb and 6.4 kb fragment hybridized to both probes confirming that each copy of AccS is linked to a copy of nptII. The 9.2 kb fragment also hybridizes to the LB. The size of the fragments are consistent with the presence of inverted T-DNA repeats at the LB and RB.

Figure 4:
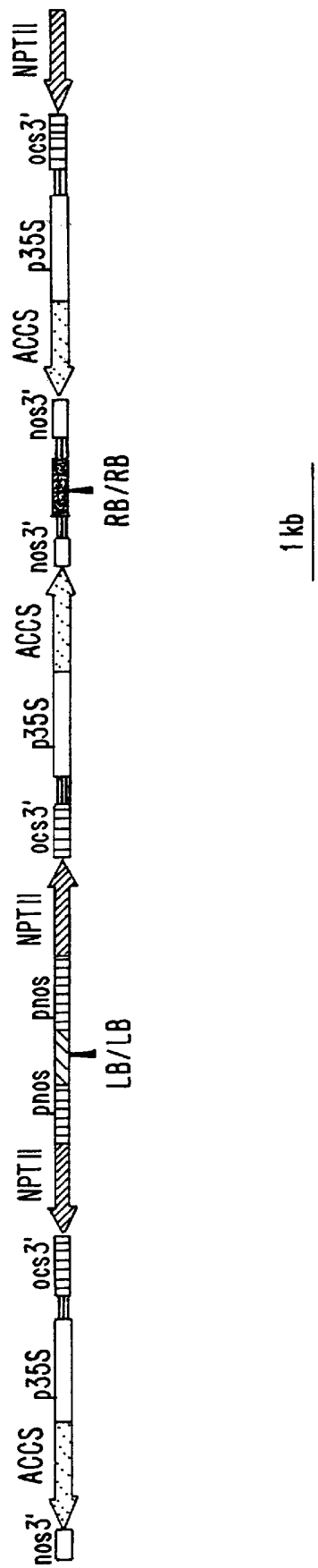
FIG. 4 is schematic diagram showing the structure of the T-DNA insert of the invention.

The structure for 1345-4 T-DNA insertion is shown in FIG. 4. It consists of three T-DNAs assembled in inverted repeats at the LB and RB. At the LB-LB and RB-RB junction, one border is deleted such that there is likely only one complete border at each junction. The LB and RB at either end of the T-DNA structure are also deleted. The endpoint rightward is internal to the nptII gene and deletes the internal NcoI site, and the endpoint leftward lies between the Acc2 gene and the right border.

Finally, the nucleotide sequence of the T-DNA insert of 1345-4 has been compiled from the deduced restriction map and is present in (SEQ ID No: 1).

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A transformed tomato plant comprising a T-DNA insert which comprises a first sequence of from about nucleotide 149 to about nucleotide 1237 of a tomato Acc synthase gene and two inverted repeats of the first sequence, the T-DNA insert having a sequence which hybridizes under stringent conditions to a nucleic acid sequence of about 15,397 base pairs comprising SEQ ID NO:1.

2. The transformed tomato plant of claim 1, wherein the plant bears fruit that reach pink stage about 2 to about 3 weeks after breaker stage, when the fruit are picked at breaker stage and stored at 15° C.

3. The transformed tomato plant of claim 1, wherein the plant bears fruit that do not reach red stage in the absence of application of ethylene.

4. The transformed tomato plant of claim 1, which is germinated from seed deposited with the American Type Culture Collection under Accession No. 97305.

5. A tomato fruit from the transformed tomato plant of claim 1.

6. A method of making a tomato plant with decreased ethylene production, the method comprising:

crossing a parent tomato plant with a transformed tomato plant comprising a T-DNA insert which comprises a first sequence of from about nucleotide 149 to about nucleotide 1237 of a tomato Acc synthase gene and two inverted repeats of the first sequence, the T-DNA insert having a sequence which hybridizes under stringent conditions to a nucleic acid sequence of about 15,397 base pairs comprising SEQ ID NO:1, thereby producing progeny.

7. The method of claim 6, wherein the tomato plant comprising the T-DNA insert is germinated from seed deposited with American Type Culture Collection Accession No. 97305.

8. The method of claim 6, further comprising the step of selecting progeny bearing fruit that reach pink stage about 2 to about 3 weeks after breaker stage, when the fruit are picked at breaker stage and stored at 15° C.

9. A tomato plant made according to the method of claim 6.

10. A transformed tomato plant comprising a genetic locus comprising:

an inserted T-DNA, comprising from the 5' to the 3' direction, a nos 3' untranslated region, a sequence consisting of nucleotide 149 to nucleotide 1237 of a tomato Acc synthase gene, a p35S promoter sequence, an ocs 3' untranslated region, a NPTII gene, a 2χpnos promotor sequence, a left border region, a 2χpnos promoter sequence, an NPTII gene, an ocs3' untranslated region, a p35S promoter sequence, a sequence consisting of nucleotide 149 to nucleotide 1237 of a tomato Acc synthase gene, a nos3' untranslated region, a right border sequence, a nos 3' untranslated region, a sequence consisting of nucleotide 149 to nucleotide 1237 of a tomato Acc synthase gene, a p35S promoter sequence, an ocs 3' untranslated region, and a NPTII gene.

11. A tomato fruit from the transformed tomato plant of claim 10.

12. A transformed tomato plant which is germinated from seed deposited with the *American type Culture Collection under Accession No.* 97305.

13. A tomato fruit from the transformed tomato plant of claim 12.

14. The transformed tomato plant of claim 10, wherein the inserted T-DNA comprises SEQ ID NO:1.

* * * * *